United States Patent [19]

Taylor, II et al.

[11] Patent Number: 5,067,491
[45] Date of Patent: Nov. 26, 1991

[54] BARRIER COATING ON BLOOD CONTACTING DEVICES

[75] Inventors: Maylon S. Taylor, II, Raleigh; Joel L. Williams, Cary, both of N.C.

[73] Assignee: Becton, Dickinson and Company, Franklin Lakes, N.J.

[21] Appl. No.: 448,034

[22] Filed: Dec. 8, 1989

[51] Int. Cl.$^5$ .......................................... A61B 5/0215
[52] U.S. Cl. ..................................... 128/748; 128/673
[58] Field of Search ........................ 128/748, 673, 675

[56] References Cited

U.S. PATENT DOCUMENTS

| | | | |
|---|---|---|---|
| 3,710,078 | 1/1973 | Huthcins, IV et al. | |
| 3,811,427 | 5/1974 | Kresse | 128/675 |
| 3,831,588 | 8/1974 | Rindner | 128/675 |
| 3,946,724 | 3/1976 | LeBalme | 128/675 |
| 4,191,193 | 3/1980 | Seo | 128/675 |
| 4,274,423 | 1/1981 | Mizuno | 128/675 |
| 4,349,467 | 9/1982 | Williams et al. | |
| 4,456,013 | 5/1984 | De Rossi | 128/748 |
| 4,722,348 | 2/1988 | Ligtenberg | 128/675 |
| 4,785,822 | 11/1988 | Wallace | |
| 4,795,446 | 1/1989 | Young | 128/675 |
| 4,796,641 | 1/1989 | Mills | 128/673 |
| 4,809,704 | 3/1989 | Sagawa | 128/675 |
| 4,886,070 | 12/1989 | Demarest | 128/675 |

FOREIGN PATENT DOCUMENTS

| | | | |
|---|---|---|---|
| 0241294 | 10/1987 | European Pat. Off. | 128/673 |
| 2420610 | 10/1975 | Fed. Rep. of Germany | 128/675 |
| 2768607 | 9/1977 | Fed. Rep. of Germany | 128/675 |

OTHER PUBLICATIONS

D. T. Delpy, A Catheter-Tip Capacitance Pressure Transducer, Jan. 1975, Biomedical Engineering, pp. 14–20.

J. M. Borky and R. D. Wise, Integrated Signal Conditioning for Silicon Pressure Sensors, IEEE Transactions on Electron Devices, Dec. 1979, pp. 1904–1910.

Troyk, Sensors Expo Proceedings, 1988, p. 308A–1.

Matsuo et al., Sensors and Activators, 9, 115 (1986).

Yasuda et al., Biomedical Sciences Instrumentation, 17, 109, (1981).

Nichols et al., Biomedical Sciences Instrumentation, 23, 57, (1987).

Kanda et al., Electronic Letters, 17, 558, (1981).

Primary Examiner—Kyle L. Howell
Assistant Examiner—Robert L. Nasser, Jr.
Attorney, Agent, or Firm—Richard E. Brown

[57] ABSTRACT

A blood pressure monitoring device includes a pressure sensing element mounted or a probe tip or in a catheter tip adapted for insertion into a patient's blood stream. The element includes a pressure transducer having a micromachined diaphragm which flexes in response to pressure changes. The flexes are converted by the transducer to electrical signals which pass back through the catheter to a display. The element and the catheter are conformally coated with a thin layer of parylene which insulates the device from the deleterious effects which blood components such as water and ions would otherwise have on various components of the device.

16 Claims, 2 Drawing Sheets

BARRIER COATING ON BLOOD CONTACTING DEVICES

BACKGROUND OF THE INVENTION

1. Field of the Invention

This invention relates to implantable biomedical devices, and more particularly, relates to blood contacting sensing devices and a method for their protection against degradation induced by the blood.

2. Background of the Invention

In current diagnostic and therapeutic medical practice, many situations arise in which an instrument must be implanted and maintained in a patient's body for extended periods of time. For example, implanted sensors for gases, electrolytes and pH which depend on a component of a body fluid reaching the sensor for a chemical reaction are well-known.

In other cases, the sensor measures a physical effect, such as blood pressure, by converting a pressure flex on the sensor to an electrical charge. In these cases, it is often essential that the body fluid be prevented from contacting the sensing element, because body fluids in general contain ions in an aqueous environment, and ions and other constituents of body fluids are often deleterious to the sensing element particularly when an electrical charge is to be developed. In addition, water vapor passes easily through most materials and itself catalyses reactions that may corrode various device components.

Exemplary of devices adapted for implantation is that described by Wallace et al. in U.S. Pat. No. 4,785,822. The Wallace et al. device includes a pressure transducer covered by a cap for monitoring pressure in body compartments such as the uterus. The transducer and cap are disposed in a flexible boot, and aligned hole in the cap and boot are filled with a silicone gel. The gel serves as a hydraulic fluid which transmits external pressure in the body compartment to the transducer and also provides a water tight seal to prevent body fluid from reaching the transducer.

Hutchins et al., in U.S. Pat. No. 3,710,781, discloses a catheter tip pressure transducer for blood pressure measurement. The transducer is covered by a rubber sheath which provides a seal against entrance of the blood into the transducer compartment.

Protection of implants from damage by body fluids has been summarized by Troyk in *Sensors Expo Proceedings*, 1988, page 308A-1. Troyk discusses the state of the art in packaging for implantable sensors, and states that, while blood compatible chemical sensors have been developed, they cannot be used with implanted systems because of packaging difficulties.

Coatings have been extensively studied for the protection of implants. Matsuo et al., in *Sensors and Activators*, 9, 115 (1986) discloses a parylene-coated reference ion sensitive field effect transistor fabricated by cleaning of the silicon surface with an oxygen plasma and depositing a 100 nm parylene coating thereon.

Yasuda et al., in *Biomedical Sciences Instrumentation*, 17, 109 (1981), reports that vapor deposited parylene coating adhere well to polymeric surfaces but poorly to metal and glass, and that the poor adhesion to metal and glass may be overcome by glow discharge depositing a primer coating of polymer and vapor depositing a coating of parylene over the polymer. Similarly, Nichols et al., in *Biomedical Sciences Instrumentation*, 23, 57 (1987), states that no single off-the-shelf polymeric material has sufficient biocompatibility and adherence to various implant materials to provide insulation to a sensor exposed to the hostile ionic environment of extracellular fluid. Thus, Nichols et al. teaches a trilayer coating for sensor implants consisting of a first glow discharge polymerized and deposited layer of methane, a second layer of glow discharge polymerized and deposited parylene C thereon and an outside layer of biocompatible parylene C vapor deposited thereon.

Blood contacting medical implants face the additional problem of the thrombogenicity associated with most foreign materials in contact with the blood. Kanda et al., in *Electronic Letters*, 17, 558 (1981) discloses a study of clotting times of various surfaces in contact with blood.

Much effort has been expended by many workers in an effort to construct a direct blood contacting device which can be implanted in a patient's blood stream and provide continuous blood pressure monitoring for a protracted period of time without sustaining damage or inducing thrombosis. While the above disclosures have addressed the problem, to date, no such device exists. The present invention provides a solution to this problem.

SUMMARY OF THE INVENTION

A pressure monitoring device includes a pressure sensing element having a pressure transducer mounted in a catheter tip. The element senses pressure changes and the transducer converts the changes to signals which are connected through the catheter to a display. The element and at least a portion of the catheter are coated conformally with a thin layer of parylene. (In the present disclosure, the term conformally means a continuous pinhole-free covering over all surfaces, joints and connections).

In a preferred device of the invention for blood pressure monitoring, the transducer is supported in an end cap affixed to the end of the catheter. The transducer is separated from a patient's blood by a micromachined diaphragm which flexes in response to changes in the blood pressure. The flexes are converted by the transducer to electrical signals which pass through a conductor, such as a wire back through the catheter to the monitor. Preferably, air communication is maintained between the interior of the catheter and the exterior surface of the diaphragm.

The preferred conformal coating of parylene is applied by vapor deposition and is from about 2 to 10μ thick.

Thus, the present invention provides a catheter tip blood pressure monitoring device in which a thin vapor-deposited pinhole-free layer of parylene is conformally coated directly onto the pressure sensing element and at least a portion of the catheter. Because the coating is very thin, it protects the sensing element without compromising the flexional properties of the diaphragm. The coating is applied directly onto the element and catheter with a need for a primer coat. Because the parylene coating adheres exceptionally firmly to the polymeric catheter and conformally covers both the catheter and the element, the coating has no tendency to delaminate from the nonpolymeric portions of the element, such as the transducer and end cap. Thus, the device may be maintained in a patient's blood stream for a week or more with swelling, cracking, leaking or delaminating. By coating a blood contacting implant with parylene in accordance with the invention, the need for an anticoagulent, such as heparin, may be eliminated for up to two weeks. On the other hand, a heparin layer may be applied to the parylene coating if desired to further enhance antithrombogenicity, particularly if the device is to remain implanted in a patient's blood stream for longer periods.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In its broadest scope, the present invention is contemplated to include any implantable sensing device conformally coated with vapor-deposited parylene directly onto the device surface. Preferred sensing devices of the invention are catheter tip sensors responsive to physical effects, such as pressure, useful for measuring pressure changes in a compartment of a living body. Particularly preferred is a catheter tip blood pressure measuring device.

A preferred parylene coated catheter tip pressure sensing device of the invention will now be described in general terms with reference to the drawings. A detailed description of the preferred device absent the parylene coating is provided in copending application, Ser. No. 410,564, filed Sept. 21, 1989, of common assignee, which copending application is herein incorporated by reference.

Figure 1:
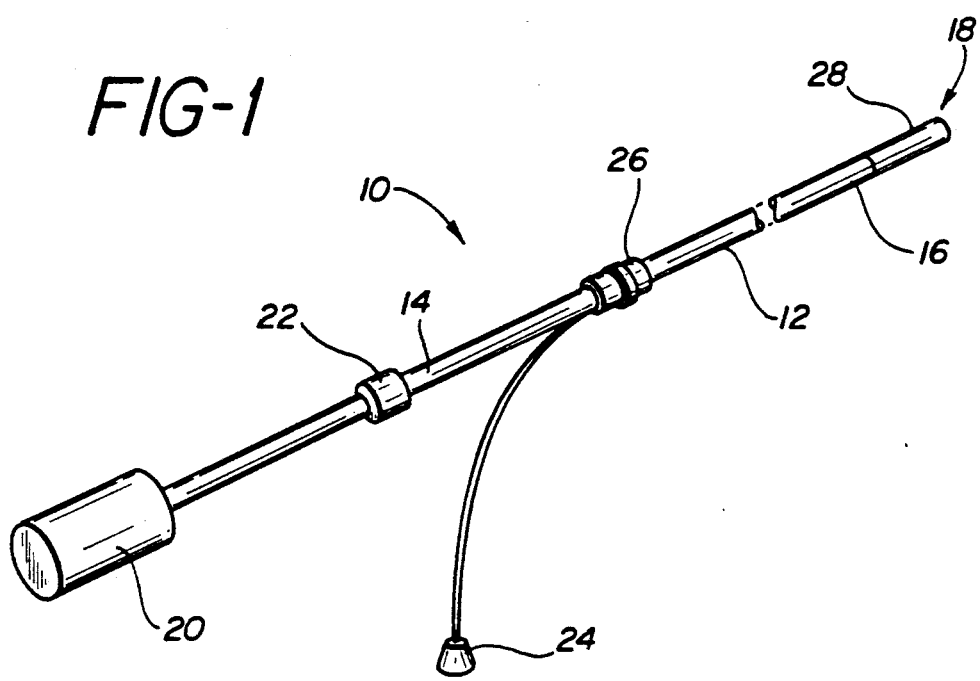
FIG. 1 is a perspective view of a blood pressure monitoring apparatus of the invention.

FIG. 1 illustrates blood pressure sensing device 10 including catheter 12 having proximal end 14 and distal end 16. A pressure sensor 18 is mounted in distal end 16, and proximal end 14 is connected to a display monitor 20. Any electronics necessary for conversion of pressure sensed by sensor 18 to the monitor may be housed in a suitable enclosure 22 between the sensor and monitor. If desired, the device may include an optional blood sample port 24 connected to the catheter by a conventional luer-lok 26. Distal end 16 of catheter 12, including that portion of the catheter which includes sensor 18, is conformally covered with a coating of parylene 28.

Figure 2:
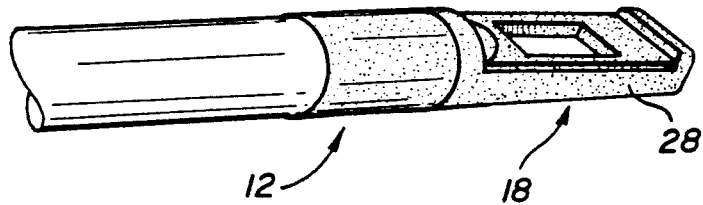
FIG. 2 is a perspective view of the catheter tip blood pressure sensor of the apparatus of FIG. 1.

FIG. 2 shows parylene coating 28 conformally covering sensor 18 and a portion of catheter 12. It is evident that the parylene coating may be applied to only a portion of the catheter, as shown in FIG. 2, or it may cover the entire portion of the catheter contemplated to be inserted into a patient.

Figure 3:
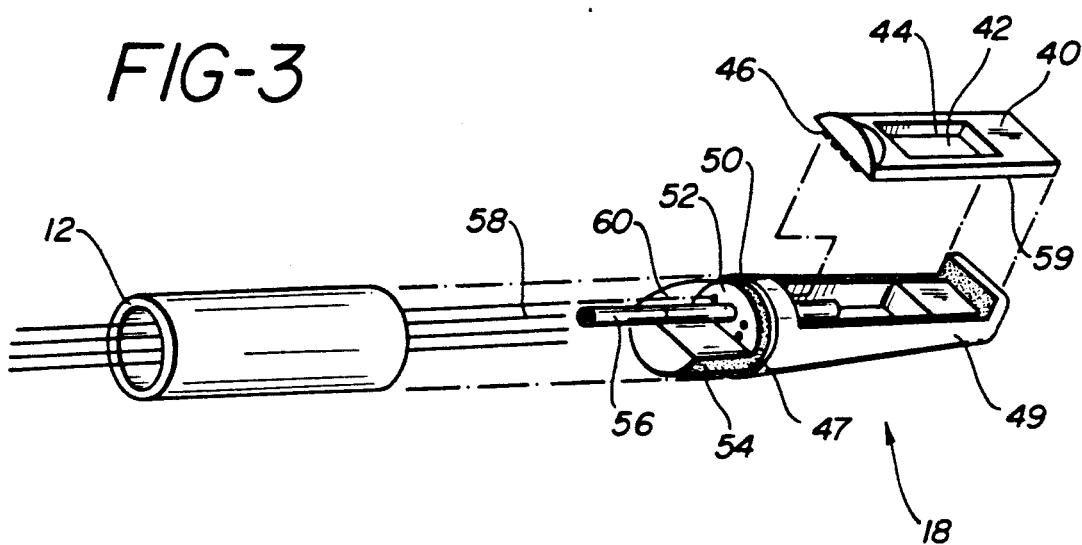
FIG. 3 is a partial cutaway view of a representative sensor suitable for coating with parylene in accordance with the invention.
Figure 4:
FIG. 4 is an optical micrograph of a control catheter probe tip cutaway to show the transducer and conductors prior to parylene coating and implantation.

FIG. 3 illustrates one embodiment of a blood pressure sensing device suitable for application of the parylene coating of the invention. Pressure sensor 18 includes a silicon transducer 40 micromachined to include a cavity 42 and a diaphragm 44 which forms the bottom wall of the transducer. A plurality of bonding pads 46 of a conducting metal are affixed to a surface of transducer 40. The transducer is affixed firmly, as for example by an adhesive 47 to an end cap 49 having a shoulder 50, a wall 52 and a flange 54. Catheter 12 may be mounted on flange 54 to abut shoulder 50 and may be affixed to both with adhesive 47.

A vent tube 56 passes through wall 52 to provide air communication for pressure equalization between the bottom surface of diaphragm 44 and the interior of catheter 12. A plurality of conductors 58 likewise pass through wall 52 and connect to bonding pads 46. A coating 59 of a suitable insulating material may be applied to a surface of transducer 40, pads 46 and conductors 58. An adhesive fill 60 may be added to the interior space bounded by flange 54 to provide support for tube 56 and conductors 58.

Any suitable polymer which can be extruded by either melt or solution techniques may be used for fabrication of catheter 12. Suitable polymers are, for example, polyethylene, polypropylene, polyvinyl acetate, polyester or preferably polyurethane or copolymers thereof.

Diaphragm 44 may be about 1 to 10, preferably about 6μ thick. While it is preferred that the diaphragm is an integral part of the silicon transducer formed by micromachining to form cavity 42, it is apparent to one skilled in the art that the diaphragm may also be a membrane of a material such as rubber.

Bonding pads 46 serve to establish electrical communication between conductors 58 and transducer 40 and may be of any conducting metal. Suitable conducting metals are silver, gold or preferably aluminum. Coating 59 may be of any suitable insulating material, preferably silicon nitride. The coating may be applied by any suitable procedure, as for example from a solvent solution followed by solvent evaporation, or, preferably it may be sputter coated to the surface of transducer 40, pads 46 and conductors 58.

End cap 49 closes the distal end of catheter 12 and provides support for transducer 40. The end cap may be ceramic or preferably a metal, most preferably stainless steel.

Conductors 58 pass through catheter 12 to provide electrical communication from transducer 40 through pads 46 to the electronics in enclosure 22. The conductors, preferably a plurality of wires, may be of any suitable material for conducting electrical signals such as platinum, copper, or, preferably aluminum. Most preferably, the conductors are coated with a layer of a suitable insulator, such as epoxy or crosslinked polyurethane.

Parylene is the generic name for thermoplastic film polymers based on para xylylene. Three precursor xylylene dimers commercially available from Nova-tran Corp., Clearlake, Wisc., may be polymerized to polymers conventionally referred to as parylene N, parylene D and parylene C, and the present invention contemplates coatings from all three. The preferred coating material of the invention is parylene C. This product is prepared by heating 2-chloro-p-xylylene in steam to a high temperature to produce a solid cyclic dimer which can be isolated in pure form. The pure dimer is then pyrolyzed to two molecules of a monomeric highly reactive intermediate α,α'-diradical of chloro-p-xylylene. On cooling, the vaporized diradical condenses on the object as a conformal coating of polymeric film in a process generally referred to as chemical vapor deposition.

The parylene coating may be deposited on the pressure sensing device of the invention in a suitable pyrolysis apparatus having a sublimination chamber, a pyrolysis chamber and a deposition chamber, as for example the Model 1050 parylene generator available from Nova-tran. The solid dimer may be placed in the sublimination chamber and the device to be coated may be placed in the deposition chamber. The apparatus may be pumped down to a pressure of about 1 to 100, preferably about 10 to 30 millitorr using a mechanical pump and a liquid nitrogen trap. The temperature of the sublimation chamber may be raised to about 50° to 300° C., preferably about 100° to 200° C., most preferably about 150° C. whereby the dimer sublimes and the vapor passes into the pyrolysis chamber. Pyrolysis of the vaporized dimer may be carried out by maintaining the temperature of the pyrolysis zone about 500° to 900° C., preferably about 600° to 800° C., most preferably about 650° C. The diradical formed by the pyrolysis passes into the deposition chamber where it polymerizes and condenses conformally on all surfaces of the device.

It has been found that the temperatures maintained in the sublimation and pyrolysis chambers and the pumpdown pressure are factors in control of the rate at which the coating forms on the device. Higher temperatures and lower pressures increase the rate of coating formation. Accordingly, coatings which range in thickness from about 0.25 to 25μ may be deposited in about 10 sec to 10 hr. Preferred coatings are about 1 to 15μ thick and are deposited in about 1 to 60 min. The most preferred coatings are about 2 to 10μ thick and are formed in about 30 min.

It is known that parylene adheres well to polymeric materials and, in accordance with the invention, it has been found that the parylene coating adheres exceptionally well to the surface of the polyurethane catheter. The firmly adhered coating on the catheter portion of the device anchors the conformal coating so that the portion of the coating on the metal end cap does not undergo any delamination in spite of the well-known failure of parylene to adhere to metal or glass surfaces.

The morphology of the parylene coatings on the catheter tip probes of the invention were analyzed by scanning electron microscopy (SEM) and found to vary in thickness from 1 to 45μ in thickness depending on the quantity of dimer charged to the sublimation zone of the reactor and the volume of the reactor. Thus, a dimer mass of 2.6 g in a 169.6 cubic inch reactor and a dimer mass of 3.1 g in a 339.3 cubic inch reaction gave a film 2 to 5μ thick.

Figure 5:
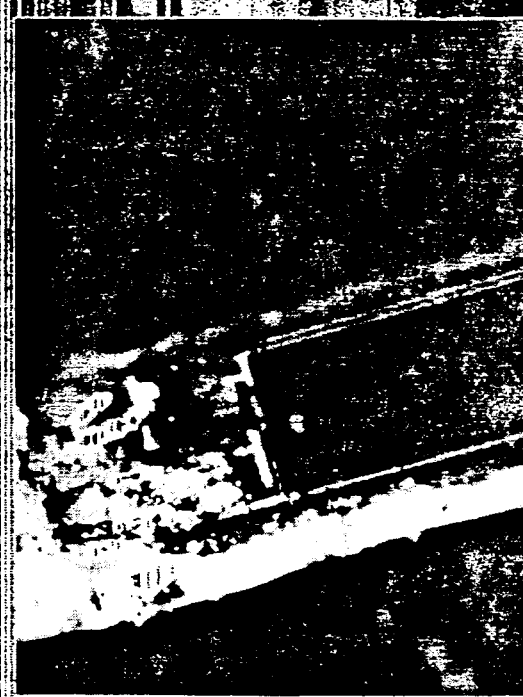
FIG. 5 is an optical micrograph of the control probe tip of FIG. 4 after 30 minutes in normal saline.
Figure 6:
FIG. 6 is an optical micrograph of the control catheter probe tip of FIG. 4 after parylene coating and eight days implantation in a rabbit artery.

In accordance with the invention, a catheter tip probe having a 2.54μ coating of parylene C, after 8 days implantation in a rabbit artery, was devoid of degradation, as described in Example III and illustrated in the photograph of FIG. 6. This probe was fully functional after the 8 days and clearly would have remained so for an indefinite period if the implantation has been maintained. In contrast, an identical probe lacking the parylene coating showed extensive decomposition after 30 minutes immersion in 1N saline, conditions which approximate blood in corrosiveness, as shown in FIG. 5.

The parylene coated probe of the invention remained substantially nonthrombogenic for the 8 day rabbit implantation. If deemed appropriate, the parylene coated probe may be coated with an anticoagulent to further protect against the formation of thrombi when placed in a patient's blood stream. A preferred anticoagulent is heparin, which may be applied by any conventional process. For example, a suitable method for heparinization of a blood contacting surface is that of Dudley et al. U.S. Pat. No. 4,349,467 in which the surface is treated sequentially with a cationic surface active agent and sodium heparin.

The following Examples are provided to further describe the invention but are not to be considered in any way as limitative of the invention.

EXAMPLE I

General Procedure for Parylene Coating

The catheter tip blood pressure probe to be parylene coated was placed in the deposition chamber of the Nova-tran Model 1050 reactor. The reactor was sealed and the appropriate amount of parylene C dimer (i.e., for a desired coating thickness) was uniformly distributed in the sublimation zone of the reactor. The system was pumped down to a partial pressure of 50 mTorr and liquid nitrogen was added to the cold trap to serve as both a trap and a cryopump. Pumping was continued until a partial pressure of 20 mTorr or less was achieved.

The pyrolysis zone heater was then turned on and the temperature raised to 655° C. over several min. The sublimation zone heater was then heated to 155° over 10 to 15 min and maintained at this temperature for 30 min. The sublimation and pyrolysis zones were cooled to room temperature, the liquid nitrogen was removed from the trap, air was bled into the system and the probes were removed. Film thickness and quality (i.e., absence of pinholes) was determined by SEM.

EXAMPLE II

The catheter tip blood pressure probe of FIGS. 2 and 3 but lacking the parylene coating was immersed in a 1N saline both for 1 hour at 37° C. The probe was removed from the bath, rinsed thoroughly with distilled water, dried and examined. An optical micrograph showed extensive degradation of the bonding pads and conductors, as shown in FIG. 5.

EXAMPLE III

A parylene-coated catheter tip blood pressure probe as illustrated in FIGS. 1-3 was inserted into the artery of a rabbit. The probe was removed after 8 days and examined visually and by SEM for degradation of the sensor element and conductors due to the blood. The probe showed no degradation, as shown in FIG. 6 and was fully functional in monitoring blood pressure.

Thus, the invention provides a catheter tip blood pressure monitoring device in which the sensitive components are protected against moisture and ions by a conformal coating of parylene firmly adhered to the polymeric catheter so that delamination of the parylene from the non-polymeric sensing element does not occur.

What is claimed is:

1. A blood pressure monitoring device comprising:

(a) A silicon pressure transducer including an integral micromachined diaphragm forming the bottom wall of said transducer, said diaphragm flexing in response to a change in blood pressure exerted on a first side of said diaphragm, said transducer converting said change in pressure to an electrical signal;

(b) a flexible polymeric tubing having said element mounted in a distal end thereof, said tubing enclosing conducting means for conducting said signal away from said transducer; and (c) a parylene coating on said transducer and at least a portion of said tubing, said coating insulating said transducer and conducting means from water vapor and ions when said device is placed in a patient's blood stream for up to eight days and longer.

2. The device of claim 1 wherein said diaphragm forms the bottom wall of said transducer.

3. The device of claim 1 wherein said transducer is a silicon chip.

4. The device of claim 1 wherein said polymeric tubing is of a polymer selected from the group consisting of polyethylene, polypropylene, polyvinyl acetate, polyester and polyurethane.

5. The device of claim 1 further comprising an end cap affixed to said distal end, said end cap having said transducer supported therein.

6. The device of claim 5 wherein said and cap is constructed of a material selected from the group consisting of ceramic and stainless steel.

7. The device of claim wherein said conducting means is a wire.

8. The device of claim 1 further comprising means providing air communication between the interior of said tubing and a second side of said diaphragm.

9. The device of claim 1 wherein said parylene coating is a vapor-deposited coating.

10. The device of claim 1 further comprising an anticoagulent on said parylene coating.

11. The device of claim 10 wherein said anticoagulent is heparin.

12. A pressure monitoring device comprising:

(a) a sensing element including a silicon transducer, said transducer converting a pressure change sensed by said element to a signal related to said pressure;

(b) a flexible polymeric tubing having said element mounted therein, said tubing enclosing means for conducting said signal away from said transducer; and (c) a parylene coating on said element and at least a portion of said tubing thereby insulating said element and means for conducting from the external environment.

13. The device of claim 12 which measures pressure in a compartment of a living body.

14. A blood pressure monitoring device comprising:

(a) a pressure sensing element including a silicon transducer having an integral micromachined diaphragm no more than 10 microns thick forming the bottom wall of said transducer, and diaphragm flexing in response to a change in pressure exerted by a patient's blood stream in contact with a first side of said diaphragm, said diaphragm converting said change in pressure to an electrical signal;

(b) a flexible polyurethane tubing having said element mounted in a distal end thereof, said tubing enclosing a wire for conducting said signal from said transducer to a display connected to a proximal end of said tubing;

(c) a conduit within said tubing establishing air communication between a second side of said diaphragm and the interior of said tubing; and (d) a parylene-C coating vapor deposited on said element and at least a portion of said tubing, said coating insulating said element and wire from water vapor and ions for up to eight days and longer when said device is placed in a patient's blood stream.

15. The device of claim 14 wherein said element further comprises an end cap affixed to said distal end and having said transducer supported therein.

16. The device of claim 14 further comprising a coating of heparin over said parylene-C coating.

* * * * *